(12) United States Patent
Hoon (10) Patent No.: US 7,829,283 B2
(45) Date of Patent: Nov. 9, 2010

(54) METHYLATION OF ESTROGEN RECEPTOR ALPHA AND USES THEREOF

(75) Inventor: Dave S. B. Hoon, Los Angeles, CA (US)

(73) Assignee: John Wayne Cancer Institute, Santa Monica, CA (US)

( * ) Notice: Subject to any disclaimer, the term of this patent is extended or adjusted under 35 U.S.C. 154(b) by 66 days.

(21) Appl. No.: 11/693,673

(22) Filed: Mar. 29, 2007

(65) Prior Publication Data

US 2008/0299551 A1 Dec. 4, 2008

Related U.S. Application Data

(60) Provisional application No. 60/787,719, filed on Mar. 29, 2006.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/23.5; 536/24.1

(58) Field of Classification Search .................. None
See application file for complete search history.

(56) References Cited

U.S. PATENT DOCUMENTS

| 7,635,561 B2 | 12/2009 | Giordano |
| 2007/0092498 A1 | 4/2007 | Giordano |

FOREIGN PATENT DOCUMENTS

WO 2005027712 A2 3/2005

OTHER PUBLICATIONS

Mori et al. Cancer Research. Jul. 1, 2006. 66(13): 6692-669.*
Martinez et al. Journal of Clinical Oncology. 2006. Supplement 1. 24 (18S) Abstract 8026.*
Nimmrich et al. Breast Cancer Research and Treatment. 2008. 111:429-437.*
Ehrlich et al. Oncogene 2002. 21: 5400-5413.*
Nishiyama et al. Cancer Biology and Therapy. 2005. 4: 440-448.*
Battagli et al. Cancer Research. Dec. 2003. 63: 8695-8699.*
Mori et al., "Predictive Utility of Circulating Methylated DNA in Serum of Melanoma Patients Receiving Biochemotherapy" Journal of Clinical Oncology, vol. 23, No. 36, pp. 9351-9358, Dec. 20, 2005.
Taback et al., "Quantification of Circulating DNA in the Plasma and Serum of Cancer Patients" Annuala of the New York Academy of Sciences, vol. 1022, pp. 17-24, 2004.
Goyal et al., "Detection of Micrometastases in Paraffin Embedded Lymph Nodes by Methylation-Specific PCT (MSP) in Patients with Breast Carcinoma" Breast Cancer Research and Treatment, vol. 82, No. Suppl. 01, p. S43, Jan. 1, 2003.
Hoon et al., "Profiling epigenetic inactivation of tumor suppressor genes in tumors and plasma from cutaneous melanoma patients" Oncogene, Nature Publishing Group, vol. 23, No. 22, pp. 4014-4022, May 13, 2004.
Yang et al., "Synergistic Activation of Functional Estrogen Receptor (ER)-alpha by DNA Methyltransferase and Histone Deacetylase Inhibition in Human ER-alpha-negative Breast Cancer Cells" Cancer Research, vol. 61, pp. 7025-7029, Oct. 1, 2001.
Mori et al., "Estrogen Receptor-alpha Methylation Predicts Melanoma Progression" Cancer Research, vol. 66, No. 13, pp. 6692-6698, Jul. 1, 2006.
European search report for corresponding European application 07754527 lists the references above.

* cited by examiner

*Primary Examiner*—Carla Myers
(74) *Attorney, Agent, or Firm*—Perkins Coie LLP (57) ABSTRACT

Methods for diagnosis, prognosis, and treatment of cancer based on the methylation status of the ER-α gene promoter are disclosed. Methylation of the ER-α gene promoter is indicative of cancer and unfavorable prognosis. The cancer can be treated with a demethylation agent.

9 Claims, 5 Drawing Sheets

SEQUENCE LISTING

<160> NUMBER OF SEQ ID NOS: 8

<210> SEQ ID NO 1
<211> LENGTH: 29
<212> TYPE: DNA
<213> ORGANISM: Artificial
<220> FEATURE:
<223> OTHER INFORMATION: Synthetic oligonucleotide

<400> SEQUENCE: 1
taaatagaga tatatcggag tttggtacg                                         29

<210> SEQ ID NO 2
<211> LENGTH: 25
<212> TYPE: DNA
<213> ORGANISM: Artificial
<220> FEATURE:
<223> OTHER INFORMATION: Synthetic oligonucleotide

<400> SEQUENCE: 2
aacttaaaat aaacgcgaaa aacga                                             25

<210> SEQ ID NO 3
<211> LENGTH: 30
<212> TYPE: DNA
<213> ORGANISM: Artificial
<220> FEATURE:
<223> OTHER INFORMATION: Synthetic oligonucleotide

<400> SEQUENCE: 3
taaatagaga tatattggag tttggtatgg                                        30

<210> SEQ ID NO 4
<211> LENGTH: 26
<212> TYPE: DNA
<213> ORGANISM: Artificial
<220> FEATURE:
<223> OTHER INFORMATION: Synthetic oligonucleotide

<400> SEQUENCE: 4
aacttaaaat aaacacaaaa aacaaa                                            26

<210> SEQ ID NO 5
<211> LENGTH: 20
<212> TYPE: DNA
<213> ORGANISM: Artificial
<220> FEATURE:
<223> OTHER INFORMATION: Synthetic oligonucleotide

<400> SEQUENCE: 5
agacatgaga gctgccaacc                                                   20

<210> SEQ ID NO 6
<211> LENGTH: 20
<212> TYPE: DNA
<213> ORGANISM: Artificial
<220> FEATURE:
<223> OTHER INFORMATION: Synthetic oligonucleotide

<400> SEQUENCE: 6
gccaggcaca ttctagaagg                                                   20

<210> SEQ ID NO 7
<211> LENGTH: 20

-continued

```
<212> TYPE: DNA
<213> ORGANISM: Artificial
<220> FEATURE:
<223> OTHER INFORMATION: Synthetic oligonucleotide

<400> SEQUENCE: 7
gggtgtgaac catgagaagt                                              20

<210> SEQ ID NO 8
<211> LENGTH: 19
<212> TYPE: DNA
<213> ORGANISM: Artificial
<220> FEATURE:
<223> OTHER INFORMATION: Synthetic oligonucleotide

<400> SEQUENCE: 8
gactgtggtc atgagtcct                                               19
```

METHYLATION OF ESTROGEN RECEPTOR ALPHA AND USES THEREOF

RELATED APPLICATION

This application claims priority to U.S. Provisional Application Ser. No. 60/787,719, filed on Mar. 29, 2006, the content of which is incorporated herein by reference in its entirety.

FUNDING

This invention was made with support in part by grants from NIH (NCI Project II P0 CA029605, CA012582, and R33-CA100314). Therefore, the U.S. government has certain rights.

FIELD OF THE INVENTION

The present invention relates in general to the ER-α (estrogen receptor alpha) gene. More specifically, the invention relates to methylation of the ER-α gene promoter and its utility in cancer diagnosis, prognosis, and treatment.

BACKGROUND OF THE INVENTION

Because it is difficult to predict which primary tumors will progress to regional or distant metastases, cutaneous melanoma remains a challenging disease to manage (1). New strategies for the identification of epigenetic biomarkers may improve the clinical management of melanoma by facilitating earlier disease diagnosis and providing more accurate prognostic information. No major study has examined the epigenetic alterations of hormone receptors in the progression from primary to metastatic melanoma in a large series of patients.

Hypermethylation of gene promoter CpG islands plays a significant role in the development and progression of various cancers, including melanoma (2-6). The identification of hypermethylated genes in tumors has become an accepted approach to assess tumor-related gene inactivation (6-9). Tumor-related gene hypermethylation in primary and metastatic melanomas was previously reported (10). Thereafter, the hypermethylation of multiple tumor-related and tumor suppressor genes during progression from primary to metastatic lesions was demonstrated (11). Several genes methylated in primary and metastatic melanomas were also detected in serum as methylated circulating DNA (11). The observation that tumor-related DNA could be detected in circulating serum provided a method of disease surveillance independent of the availability of gross tumor tissue (12-17).

ER-α belongs to a superfamily of transcription activators (18, 19) involved in many physiological processes, including tumor progression (20-22). Loss of ER-α expression has been associated with aberrant CpG island hypermethylation in breast cancer cell lines and tumors (23-27), and shown to modulate breast cancer progression (5). Several studies have reported the presence of estrogen receptor in melanoma cell lines, but analysis of human melanomas have shown variable ER-α expression (28-31). Several in vitro experiments established that tamoxifen is an effective growth inhibitor of melanoma cells (32, 33). Based on the variable presence of ER-α in melanoma cells, as well as anecdotal reports of clinical responses to anti-estrogen therapy, several studies of hormonal and chemohormonal treatments were coordinated. Initial trials were encouraging, with improved response rates and median overall survival in patients, receiving tamoxifen, particularly women (34, 35). Subsequent trials, however, failed to show significant differences in response rates or overall survival when tamoxifen was used alone or in combination with systemic therapies (36-42). Reasons for the discrepancies in response to anti-estrogen therapy between these trials are unknown.

SUMMARY OF THE INVENTION

This invention relates to the utility of methylation of the ER-α gene promoter in diagnosis, prognosis, and treatment of cancer.

In one aspect, the invention provides methods for diagnosis and prognosis of cancer based on methylation of the ER-α gene promoter in acellular DNA in a body fluid of a subject.

More specifically, the invention features a method of determining whether a subject is suffering from cancer. The method comprises (1) providing a body fluid sample from a subject, wherein the sample contains DNA that exists as acellular DNA in the body fluid; and (2) determining the methylation level of the ER-α gene promoter in the DNA. The methylation level of the ER-α gene promoter in the DNA, if higher than a control methylation level, indicates that the subject is likely to be suffering from cancer.

The invention also features a method of determining the outcome of cancer. The method comprises (1) providing a body fluid sample from a subject suffering from cancer, wherein the sample contains DNA that exists as acellular DNA in the body fluid; and (2) determining the methylation level of the ER-α gene promoter in the DNA. The methylation level of the ER-α gene promoter in the DNA, if higher than a control methylation level, indicates that the subject is likely to have an unfavorable outcome of the cancer. In one embodiment, the higher methylation level of the ER-α gene promoter in the DNA is indicative of a decreased response to a cancer therapy, progression-free survival, or overall survival.

In the methods described above, the cancer may be melanoma, colorectal cancer, pancreatic cancer, hepatacellular cancer, esophageal cancer, sarcoma, lung cancer, breast cancer, or gastric cancer; the cancer may be a primary or metastatic cancer; the sample may be a serum, plasma, peritoneal/pleural, or cerebral spinal sample.

In another aspect, the invention provides a method for prognosis of cancer based on methylation of the ER-α gene promoter in cellular DNA contained in a PE (paraffin-embedded) cancer tissue sample of a subject. More specifically, the invention features a method of determining the outcome of cancer. The method comprises (1) providing a PE cancer tissue sample of a subject, wherein the sample contains cellular DNA; and (2) determining the methylation level of the ER-α gene promoter in the DNA. The methylation level of the ER-α gene promoter in the DNA, if higher than a control methylation level, indicates that the subject is likely to have an unfavorable outcome of the cancer. In this method, the cancer may be melanoma, colorectal cancer, pancreatic cancer, hepatacellular cancer, esophageal cancer, sarcoma, lung cancer, breast cancer, or gastric cancer; the cancer may be a primary or metastatic cancer.

In addition, the invention provides a method for prognosis of cancer based on methylation of the ER-α gene promoter in cellular DNA contained in a cancer tissue or cancer cells in a body fluid from a subject. More specifically, the invention features a method of determining the outcome of cancer. The method comprises (1) providing a cancer tissue sample or a body fluid sample from a subject, wherein the sample contains cellular DNA, the body fluid contains cancer cells, and the subject is suffering from melanoma, pancreatic cancer, hepatacellular cancer, esophageal cancer, sarcoma, or gastric cancer; and (2) determining the methylation level of the ER-α gene promoter in the DNA. The methylation level of the ER-α gene promoter in the DNA, if higher than a control methylation level, indicates that the subject is likely to have an unfavorable outcome of the melanoma, pancreatic cancer, hepatacellular cancer, esophageal cancer, sarcoma, or gastric cancer. In this method, the melanoma, pancreatic cancer, hepatacellular cancer, esophageal cancer, sarcoma, or gastric cancer may be primary or metastatic melanoma, pancreatic cancer, hepatacellular cancer, esophageal cancer, sarcoma, or gastric cancer.

Also within the invention is a method of treating cancer by reducing methylation of the ER-α gene promoter in a cell. More specifically, the invention features a method of reducing DNA methylation in a cell, comprising contacting a melanoma, pancreatic cancer, hepatacellular cancer, esophageal cancer, sarcoma, or gastric cancer cell with a demethylation agent (e.g., 5-aza-2-deoxycytidine), thereby reducing methylation of the ER-α gene promoter in the cell. The method may further comprise contacting the cell with a histone deacetylase inhibitor such as trichostatin A. In this method, the melanoma, pancreatic cancer, hepatacellular cancer, esophageal cancer, sarcoma, or gastric cancer may be primary or metastatic melanoma, pancreatic cancer, hepatacellular cancer, esophageal cancer, sarcoma, or gastric cancer.

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

BRIEF DESCRIPTION OF THE FIGURES

FIG. 4 illustrates representative MSP results of sera and tissue specimens. No methylation peak appeared in serum of healthy donor (a). A methylation peak appeared in normal liver tissue (b). A single methylation peak was detected in sera and PE specimens from stage IV melanoma patients (c-h). Figures e and f are paired specimens from the same patient.

DETAILED DESCRIPTION OF THE INVENTION

The role of ER-α in melanoma is unknown. Mechanisms regulating the expression of ER-α in melanoma are poorly defined; to date, no mutation or other gross structural alteration of the ER-α gene has been reported in melanoma.

The invention is based at least in part upon the unexpected discovery that ER-α gene silencing via gene promoter hypermethylation in primary and metastatic melanoma plays an important role in melanoma progression, and can be used as a prognostic molecular biomarker. More specifically, ER-α hypermethylation in primary and metastatic melanomas and sera as a potential tumor progression marker was assessed. ER-α methylation status in tumor (n=107) and sera (n=109) from AJCC stage I-IV melanoma patients was examined by MSP. The clinical significance of serum methylated ER-α was assessed among AJCC stage IV melanoma patients receiving BC with tamoxifen. Rates of ER-α methylation in AJCC stage I, II, and III primary melanomas were 36% (4 of 11), 26% (5 of 19), and 35% (8 of 23), respectively. Methylated ER-α was detected in 42% (8 of 19) of stage III and 86% (30 of 35) of stage IV metastatic melanomas. ER-α was methylated more frequently in metastatic than primary melanomas (p=0.0003). Of 109 melanoma patients' sera in AJCC stage I, II, III, and IV, methylated ER-α was detected in 10% (2 of 20), 15% (3 of 20), 26% (5 of 19), and 32% (16 of 50), respectively. Serum methylated ER-α was detected more frequently in advanced than localized melanomas (p=0.03) and was the only factor predicting progression-free (RR 2.64, 95% confidence interval (CI) 1.36-5.13, p=0.004) and overall survival (RR 2.31, 95% CI 1.41-5.58, p=0.003) in BC patients. Hypermethylated ER-α is a significant factor in melanoma progression. Serum methylated ER-α is an unfavorable prognostic factor.

Accordingly, the invention provides various methods for cancer diagnosis, prognosis, and treatment. A diagnostic method of the invention generally involves analyzing the methylation level of the ER-α gene promoter in a biological sample from a subject. If the methylation level of the ER-α gene promoter in the sample is higher than a control value, the subject is likely to be suffering from cancer.

One diagnostic method of the invention involves a body fluid sample from a subject. The sample contains DNA that exists as acellular DNA in the body fluid. The methylation level of the ER-α gene promoter in the DNA is determined. If the methylation level of the ER-α gene promoter in the DNA is higher than a control methylation level, the subject is likely to be suffering from cancer.

As used herein, a "subject" refers to a human or animal, including all mammals such as primates (particularly higher primates), sheep, dog, rodents (e.g., mouse or rat), guinea pig, goat, pig, cat, rabbit, and cow. In a preferred embodiment, the subject is a human. In another embodiment, the subject is an experimental animal or animal suitable as a disease model.

The term "body fluid" refers to any body fluid in which acellular DNA or cells (e.g., cancer cells) may be present, including, without limitation, blood, serum, plasma, bone marrow, cerebral spinal fluid, peritoneal/pleural fluid, lymph fluid, ascite, serous fluid, sputum, lacrimal fluid, stool, and urine. "Acellular DNA" refers to DNA that exists outside a cell in a body fluid of a subject or the isolated form of such DNA, while "cellular DNA" refers to DNA that exists within a cell or is isolated from a cell.

Body fluid samples can be obtained from a subject using any of the methods well known in the art. Methods for extracting acellular DNA from these samples are also well known in the art. Commonly, acellular DNA in a body fluid sample is separated from cells, precipitated in alcohol, and dissolved in an aqueous solution.

A "promoter" is a region of DNA extending 150-300 bp upstream from the transcription start site that contains binding sites for RNA polymerase and a number of proteins that regulate the rate of transcription of the adjacent gene. The promoter region of the ER-α gene is well known in the art. Methylation of the ER-α gene promoter can be assessed by any method commonly used in the art, for example, MSP, bisulfite sequencing, or pyrosequencing.

MSP is a technique whereby DNA is amplified by PCR dependent upon the methylation state of the DNA. See, e.g., U.S. Pat. No. 6,017,704. Determination of the methylation state of a nucleic acid includes amplifying the nucleic acid by means of oligonucleotide primers that distinguish between methylated and unmethylated nucleic acids. MSP can rapidly assess the methylation status of virtually any group of CpG sites within a CpG island, independent of the use of methylation-sensitive restriction enzymes. This assay entails initial modification of DNA by sodium bisulfite, converting all unmethylated, but not methylated, cytosines to uracils, and subsequent amplification with primers specific for methylated versus unmethylated DNA. MSP requires only small quantities of DNA, is sensitive to 0.1% methylated alleles of a given CpG island locus, and can be performed on DNA extracted from body fluid, tissue, and PE samples. MSP eliminates the false positive results inherent to previous PCR-based approaches which relied on differential restriction enzyme cleavage to distinguish methylated from unmethylated DNA. This method is very simple and can be used on small amounts of tissue or few cells and fresh, frozen, or PE sections. MSP product can be detected by gel electrophoresis, CAE (capillary array electrophoresis), or real-time quantitative PCR.

Bisulfite sequencing is widely used to detect 5-MeC (5-methylcytosine) in DNA, and provides a reliable way of detecting any methylated cytosine at single-molecule resolution in any sequence context. The process of bisulfite treatment exploits the different sensitivity of cytosine and 5-MeC to deamination by bisulfite under acidic conditions, in which cytosine undergoes conversion to uracil while 5-MeC remains unreactive.

To determine whether a subject (i.e., a test subject) is suffering from cancer, the methylation level of the ER-α gene promoter in the acellular DNA of the test subject is compared with a control value. A suitable control value may be, e.g., the methylation level of the ER-α gene promoter in acellular DNA from a body fluid of a normal subject. If the methylation level of the ER-α gene promoter in the acellular DNA from the test subject is higher than the control value, the test subject is likely to be suffering from cancer.

As used herein, "cancer" refers to a disease or disorder characterized by uncontrolled division of cells and the ability of these cells to spread, either by direct growth into adjacent tissue through invasion, or by implantation into distant sites by metastasis. Exemplary cancers include, but are not limited to, primary cancer, metastatic cancer, AJCC stage I, II, III, or IV cancer, carcinoma, lymphoma, leukemia, sarcoma, mesothelioma, glioma, germinoma, choriocarcinoma, prostate cancer, lung cancer, breast cancer, colorectal cancer, gastrointestinal cancer, bladder cancer, pancreatic cancer, endometrial cancer, ovarian cancer, melanoma, brain cancer, testicular cancer, kidney cancer, skin cancer, thyroid cancer, head and neck cancer, hepatacellular cancer, esophageal cancer, gastric cancer, intestinal cancer, colon cancer, rectal cancer, myeloma, neuroblastoma, and retinoblastoma. Preferably, the cancer is a cancer associated with the biological function of the ER-α gene, such as melanoma, colorectal cancer, pancreatic cancer, hepatacellular cancer, esophageal cancer, sarcoma, lung cancer, breast cancer, and gastric cancer.

A prognostic method of the invention generally involves analyzing the methylation level of the ER-α gene promoter in a biological sample from a subject suffering from cancer. If the methylation level of the ER-α gene promoter in the sample is higher than a control value, the subject is likely to have an unfavorable outcome of the cancer. For instance, the subject may have a decreased response to a cancer therapy such as BC, progression-free survival, or overall survival.

One prognostic method of the invention involves a body fluid sample from a subject suffering from cancer. The sample contains DNA that exists as acellular DNA in the body fluid. Another prognostic method of the invention involves a PE cancer tissue sample of a subject. The sample contains cellular DNA. In both methods, the methylation level of the ER-α gene promoter in the DNA is determined. If the methylation level of the ER-α gene promoter in the DNA is higher than a control methylation level, the subject is likely to have an unfavorable outcome of the cancer.

A third prognostic method of the invention involves a cancer tissue sample or a body fluid sample from a subject. The sample contains cellular DNA. The body fluid contains cancer cells. The subject is suffering from melanoma, pancreatic cancer, hepatacellular cancer, esophageal cancer, sarcoma, or gastric cancer. The methylation level of the ER-α gene promoter in the DNA is determined. If the methylation level of the ER-α gene promoter in the DNA is higher than a control methylation level, the subject is likely to have an unfavorable outcome of the melanoma, pancreatic cancer, hepatacellular cancer, esophageal cancer, sarcoma, or gastric cancer.

A tissue sample from a subject may be a biopsy specimen sample, a normal or benign tissue sample, a cancer or tumor tissue sample, a freshly prepared tissue sample, a frozen tissue sample, a PE tissue sample, a primary cancer or tumor sample, or a metastasis sample. Exemplary tissues include, but are not limited to, epithelial, connective, muscle, nervous, heart, lung, brain, eye, stomach, spleen, bone, pancreatic, kidney, gastrointestinal, skin, uterus, thymus, lymph node, colon, breast, prostate, ovarian, esophageal, head, neck, rectal, testis, throat, thyroid, intestinal, melanocytic, colorectal, hepatacellular, gastric, and bladder tissues.

To practice the prognostic methods of the invention, acellular DNA can be obtained using the methods described above. Tissue samples can be obtained from a subject using any of the methods well known in the art. Methods for extracting cellular DNA from tissue and body fluid samples are also well known in the art. Typically, cells are lysed with detergents. After cell lysis, proteins are removed from DNA using various proteases. DNA is then extracted with phenol, precipitated in alcohol, and dissolved in an aqueous solution.

The methylation level of the ER-α gene promoter in acellular and cellular DNA can be determined using the methods described above and compared with corresponding control values. As mentioned above, a control value for the methylation level of the ER-α gene promoter in the acellular DNA of a test subject may be, e.g., the methylation level of the ER-α gene promoter in acellular DNA from a body fluid of a normal subject. A control value for the methylation level of the ER-α gene promoter in the cellular DNA of a test subject may be, e.g., the methylation level of the ER-α gene promoter in cellular DNA from a cell line, a tissue, or cells in a body fluid where methylation of the ER-α gene promoter is non-detectable. Preferably, the control cell line is a cancer cell line and the control tissue is a cancer tissue, where the control cell line, the control tissue, and the cancer tissue from the test subject are of the same cancer type. The methylation level of the ER-α gene promoter in the DNA from the test subject, if higher than the control value, is indicative of an unfavorable outcome of cancer.

The discovery that the ER-α gene promoter is methylated in melanoma, pancreatic cancer, hepatacellular cancer, esophageal cancer, sarcoma, and gastric cancer cells is useful for identifying compounds for treating melanoma, pancreatic cancer, hepatacellular cancer, esophageal cancer, sarcoma, and gastric cancer. For example, a melanoma, pancreatic cancer, hepatacellular cancer, esophageal cancer, sarcoma, or gastric cancer cell may be contacted with a test compound. The methylation levels of the ER-α gene promoter in the cell prior to and after the contacting step are compared. If the methylation level of the ER-α gene promoter in the cell decreases after the contacting step, the test compound is identified as a candidate compound for treating melanoma, pancreatic cancer, hepatacellular cancer, esophageal cancer, sarcoma, or gastric cancer.

Similarly, a subject suffering from melanoma, pancreatic cancer, hepatacellular cancer, esophageal cancer, sarcoma, or gastric cancer may be contacted with a test compound. Samples of cancer tissues or body fluids containing cancer cells or acellular DNA are obtained from the subject. The methylation level of the ER-α gene promoter in cellular or acellular DNA in a sample obtained from the subject prior to the contacting step is compared with the methylation level of the ER-α gene promoter in cellular or acellular DNA in a sample obtained from the subject after the contacting step. If the methylation level of the ER-α gene promoter in cellular or acellular DNA decreases after the contacting step, the test compound is identified as a candidate compound for treating melanoma, pancreatic cancer, hepatacellular cancer, esophageal cancer, sarcoma, or gastric cancer.

The test compounds of the present invention can be obtained using any of the numerous approaches (e.g., combinatorial library methods) known in the art. See, e.g., U.S. Pat. No. 6,462,187. Such libraries include, without limitation, peptide libraries, peptoid libraries (libraries of molecules having the functionalities of peptides, but with a novel, non-peptide backbone that is resistant to enzymatic degradation), spatially addressable parallel solid phase or solution phase libraries, synthetic libraries obtained by deconvolution or affinity chromatography selection, and the "one-bead one-compound" libraries. Compounds in the last three libraries can be peptides, non-peptide oligomers, or small molecules. Examples of methods for synthesizing molecular libraries can be found in the art. Libraries of compounds may be presented in solution, or on beads, chips, bacteria, spores, plasmids, or phages.

The candidate compounds so identified, as well as compounds known to demethylate DNA (i.e., demethylation agents such as 5-Aza) in a cell or subject, can be used to demethylate the ER-α gene promoter in melanoma, pancreatic cancer, hepatacellular cancer, esophageal cancer, sarcoma, and gastric cancer cells in vitro and in vivo. In one embodiment, the method involves contacting a melanoma, pancreatic cancer, hepatacellular cancer, esophageal cancer, sarcoma, or gastric cancer cell with a demethylation agent, thereby reducing methylation of the ER-α gene promoter in the cell. To treat a subject suffering from melanoma, pancreatic cancer, hepatacellular cancer, esophageal cancer, sarcoma, or gastric cancer, an effective amount of a demethylation agent is administered to the subject to reduce the methylation level of the ER-α gene promoter in the subject. A subject to be treated may be identified in the judgment of the subject or a health care professional, and can be subjective (e.g., opinion) or objective (e.g., measurable by a test or diagnostic method such as those described above).

A "treatment" is defined as administration of a substance to a subject with the purpose to cure, alleviate, relieve, remedy, prevent, or ameliorate a disorder, symptoms of the disorder, a disease state secondary to the disorder, or predisposition toward the disorder.

An "effective amount" is an amount of a compound that is capable of producing a medically desirable result in a treated subject. The medically desirable result may be objective (i.e., measurable by some test or marker) or subjective (i.e., subject gives an indication of or feels an effect).

In some embodiments, a melanoma, pancreatic cancer, hepatacellular cancer, esophageal cancer, sarcoma, or gastric cancer cell or a subject suffering from melanoma, pancreatic cancer, hepatacellular cancer, esophageal cancer, sarcoma, or gastric cancer is further treated with other compounds or radiotherapy. For example, one type of other compounds are HDAC (histone deacetylase) inhibitors such as TSA (trichostatin A) which can modify histones in chromatin regions and activate genes silenced by methylation of CpG islands in promoter regions.

For treatment of cancer, a compound is preferably delivered directly to tumor cells, e.g., to a tumor or a tumor bed following surgical excision of the tumor, in order to treat any remaining tumor cells. For prevention of cancer invasion and metastases, the compound can be administered to, for example, a subject that has not yet developed detectable invasion and metastases but is found to have increased methylation level of the ER-α gene promoter.

The compounds of the invention can be incorporated into pharmaceutical compositions. Such compositions typically include the compounds and pharmaceutically acceptable carriers. "Pharmaceutically acceptable carriers" include solvents, dispersion media, coatings, antibacterial and antifungal agents, isotonic and absorption delaying agents, and the like, compatible with pharmaceutical administration.

A pharmaceutical composition is formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

In one embodiment, the compounds are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form," as used herein, refers to physically discrete units suited as unitary dosages for the subject to be treated, each unit containing a predetermined quantity of an active compound calculated to produce the desired therapeutic effect in association with the required pharmaceutical carrier.

The dosage required for treating a subject depends on the choice of the route of administration, the nature of the formulation, the nature of the subject's illness, the subject's size, weight, surface area, age, and sex, other drugs being administered, and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE I

ER-α Methylation Predicts Melanoma Progression

Materials and Methods

Melanoma Cell Line and Tumor DNA Isolation

DNA was extracted from 11 melanoma cell lines established from metastatic tumors at John Wayne Cancer Institute (JWCI) and one breast cancer cell line (MCF-7) from American Type Culture Collection (ATCC) (Manassas, Va.) as described previously (14). Institutional Review Board approval for the use of human tissues was obtained from Saint John's Health Center and JWCI prior to beginning the study. Patients who underwent surgery for AJCC stage I, II, III, and IV melanoma (11 stage I primary tumors; 19 stage II primary tumors; 23 stage III primary tumors; 19 stage III metastatic tumors; and 35 stage IV metastatic tumors) were selected consecutively by the database coordinator from the institutional melanoma patient and specimen database (Table 1A). PE tumor specimens from these patients were obtained from the Division of Surgical Pathology at Saint John's Health Center.

TABLE 1A

Clinical characteristics of melanoma patients

| Patient Characteristics |  | n (%) |
|---|---|---|
| Total patients (tissue) |  | 107 |
| Sex | male | 58 (54%) |
|  | female | 49 (46%) |
| Age (median) | <50 | 25 (23%) |
|  | ≧60 | 50 (47%) |
| Stage | I | 11 (10%) |
|  | II | 19 (18%) |
|  | III (primary) | 23 (21%) |
|  | III (metastasis) | 19 (18%) |
|  | IV (metastasis) | 35 (33%) |
| Total patients (serum) |  | 109 |
| Sex | male | 73 (67%) |
|  | female | 34 (31%) |
|  | unknown | 2 (2%) |
| Age (median 45) | <50 | 43 (41%) |
|  | ≧60 | 51 (48%) |
| Stage | I | 20 (19%) |
|  | II | 20 (19%) |
|  | III | 19 (18%) |
|  | IV | 50 (48%) |

Several 8-μm sections were cut from formalin-fixed, PE blocks as described previously (43). One section from each tumor block was deparaffinized, mounted on a glass slide, and stained with hematoxylin and eosin for microscopic analysis. Light microscopy was used to confirm tumor location and assess tissue homogeneity. Additional sections from the tumor block were mounted on glass slides and microdissected under light microscopy. Dissected tissues were digested with 50 μl of proteinase K-containing lysis buffer at 50° C. for 12 hr, followed by heat deactivation of proteinase K at 95° C. for 10 min (5). DNA was extracted as previously described (10).

Serum DNA Isolation

AJCC stage I (n=20), stage II (n=20), stage III (n=19), and stage IV patients (n=50) diagnosed with melanoma were assessed for this study (Table 1A). Stage I, II, and III patients received no additional adjuvant therapy, but stage IV patients received a systemic concurrent BC regimen of dacarbazine (DTIC) or temazolamide, cisplatin, vinblastine, interferon α-2b, interleukin-2 (IL-2), and tamoxifen in the setting of one of several phase II trials, as previously reported (40-42).

AJCC stage IV patients (Table 1B) were selected and coded by the clinical study coordinator and assessed in laboratory and statistical analyses in a blinded fashion. The selection of stage IV patients was based on patient response or non-response to BC, availability of clinical follow-up data, completion of the BC trial, and specimen availability. Patients were categorized as responders or non-responders to BC based on clinical response criteria (42). Those showing a complete response (CR, n=13) or partial response (PR, n=10) were included in the responder group (n=23), whereas patients demonstrating progressive disease (PD, n=24) were deemed non-responders. Patients exhibiting stable disease (SD, n=3) were considered neither responders nor non-responders. One patient in the responder group was lost to follow-up and excluded from the survival analysis. Serum drawn from healthy donors (n=40) served as normal controls.

TABLE 1B

Clinical demographics of stage IV melanoma
patients receiving biochemotherapy

| Patient Characteristics (serum donors) | | n (%) |
|---|---|---|
| Total patients | | 50 |
| Sex | male | 38 (76%) |
| | female | 12 (24%) |
| Age (median 45) | <50 | 34 (68%) |
| | ≧60 | 16 (32%) |
| ECOG | 0 | 14 (28%) |
| | 1 | 12 (24%) |
| | 2 | 24 (48%) |
| BC response | | |
| Responder | CR | 13 (26%) |
| | PR | 10 (20%) |
| Non-responder | PD | 24 (48%) |

Stage IV patients' blood was drawn for serum prior to administration of BC. Ten ml of blood was collected in serum separator tubes, centrifuged, run through a 13-mm serum filter (Fisher Scientific, Pittsburgh, Pa.), aliquoted, and cryopreserved at −30° C. DNA was extracted and processed from serum as previously described (6). DNA quantification was performed on all serum specimens using the PicoGreen quantification assay (Molecular Probes, Eugene, Oreg.) (44).

Cell Line and Tissue DNA Sodium Bisulfite Modification

Extracted DNA from cell lines and PE melanoma tumors was subjected to sodium bisulfite modification (11). Briefly, 2 µg DNA was denatured in 0.3 M NaOH for 3 min at 95° C. and then 550 µl of a 2.5 M sodium bisulfite/125 mM hydroquinone solution was added. Samples were incubated under mineral oil in the dark for 3 hr at 60° C. Salts were removed using the Wizard DNA Clean-Up System (Promega, Madison, Wis.) and desulfonated in 0.3 M NaOH at 37° C. for 15 min. Modified DNA was precipitated with ethanol using Pellet Paint NF (Novagen, Madison, Wis.) as a carrier and resuspended in molecular grade $H_2O$. DNA samples were cryopreserved at −30° C. until MSP was performed.

Serum DNA Sodium Bisulfite Modification

Extracted DNA from serum was subjected to sodium bisulfite modification (44). Briefly, DNA from 500 µl of serum was supplemented with 1 µg salmon sperm DNA (Sigma, St. Louis, Mo.) and denatured in 0.3 M NaOH for 3 min at 95° C. Overall, 550 µl of a 2.5 M sodium bisulfite/125 mM hydroquinone solution was added. Samples were incubated under mineral oil in the dark for 3 hr at 60° C. Salts were removed using the Wizard DNA Clean-Up System (Promega, Madison, Wis.) and desulfonated in 0.3 M NaOH at 37° C. for 15 min. Modified serum DNA was prepared and stored identically to tissue samples.

Detection of Methylated ER-α

ER-α methylation status was assessed using two sets of fluorescent labeled primers specifically designed to amplify methylated or unmethylated DNA sequences of the ER-α promoter region. Primer sequences are provided as methylated sense and antisense followed by unmethylated sense and antisense sequences, with annealing temperatures and PCR product size: ER-α methylated-specific forward, 5'-TAAATAGAGATATATCGGAGTTTGGTACG-3' (SEQ ID NO: 1) and reverse, 5'-AACTTAAAATAAACGC-GAAAAACGA-3' (SEQ ID NO: 2) (61° C., 96 bp); unmethylated-specific forward, 5'-TAAATAGAGATATATTG-GAGTTTGGTATGG-3' (SEQ ID NO: 3) and reverse, 5'-AACTTAAAATAAACACAAAAAACAAA-3' (SEQ ID NO: 4) (58° C., 96 bp). Bisulfite-modified DNA was subjected to PCR amplification in a final reaction volume of 20 µl containing PCR buffer, 2.5 mM $MgCl_2$, dNTPs, 0.3 µM primers, and 0.5 U of AmpliTaq Gold DNA polymerase (Applied Biosystems, Foster, Calif.). PCR was performed with an initial incubation at 95° C. for 10 min, followed by 40 cycles of denaturation at 95° C. for 30 sec, annealing for 30 sec, extension at 72° C. for 30 sec, and final hold at 72° C. for 7 min. DNA from the ER-α positive breast cancer cell line MCF-7 was used as a control to verify the presence of ER-α. DNA from the ER-α negative melanoma cell line MCA was used as a control to verify the absence of ER-α. A universal unmethylated control was synthesized from normal DNA by phi-29 DNA polymerase and served as a positive unmethylated control (45). Unmodified lymphocyte DNA was used as a negative control for methylated and unmethylated reactions. SssI methylase (New England Bio Labs, Beverly, Mass.) treated lymphocyte DNA was used as a positive methylated control. PCR products were visualized using CAE (CEQ 8000XL; Beckman Coulter, Inc., Fullerton, Calif.) in a 96-well microplate format (6). Methylated and unmethylated PCR products from each sample were assessed simultaneously using forward primers labeled with Beckman Coulter WellRED dye-labeled phosphoramidites (Genset oligos, Boulder, Colo.). Forward methylated-specific primers were labeled with D4pa dye, and forward unmethylated-specific primers were labeled with D2a dye. One µl methylated PCR product and 1 µl unmethylated PCR product were mixed. with 40 µl loading buffer and a 0.5 µl dye-labeled size standard (Beckman Coulter, Inc., Fullerton, Calif.). Each marker was optimized with methylated and unmethylated controls. Samples demonstrating a peak at the base pair size marker for unmethylated DNA were considered unmethylated, while those demonstrating a peak at the base pair size marker for methylated DNA were considered methylated.

5-Aza and TSA Treatment of Melanoma Cell Lines

To confirm down-regulation of ER-α expression by hypermethylation of the ER-α promoter region, cell lines were treated with the DNA-demethylating agent, 5-Aza, and the HDAC inhibitor, TSA. In combination with 5-Aza treatment, TSA can up-regulate the mRNA expression of genes silenced due to hypermethylation (26, 27). The MCF-7 cell line was used as an ER-α positive control and the MCA cell line was used as an ER-α negative control. Cell lines were maintained in RPMI 1640 medium supplemented with heat-inactivated 10% fetal bovine serum (FBS), penicillin G, and streptomycin (100 U/ml). Cells were treated with 1000 nM TSA for 24 hr (Wako Biochemicals, Osaka, Japan) and 1000 nM 5-Aza for five days (Sigma Chemical Co., St Louis, Mo.). After treatment with 5-Aza and TSA, melanoma cells were washed with phosphate buffered saline (PBS) and harvested with 0.25% trypsin-0.53 mM EDTA (Gibco, Auckland, N.J.). The mRNA expression level of ER-α was assessed by RT-PCR before and after 5-Aza and TSA treatment.

mRNA Analysis

Total cellular RNA from melanoma cell lines was extracted using Tri-Reagent (Molecular Research Center, Inc., Cincinnati, Ohio) as previously described (6). The RNA was quantified and assessed for purity using ultraviolet spectrophotometry and the RIBOGreen detection assay (Molecular Probes, Eugene, Oreg.). The expression of mRNA for GAPDH, an internal reference housekeeping gene, was assessed by RT-PCR on all RNA samples to verify the integrity of RNA and to indicate equal loading of PCR products for gel electrophoresis.

All RT reactions were performed using Moloney murine leukemia virus reverse-transcriptase (Promega, Madison, Wis.) with oligo-dT (GeneLink, Hawthorne, N.Y.) priming as previously described (6). cDNA from 250 ng of total RNA was used for each reaction (46). The RT-PCR reaction mixture consisted of 1 µM of each primer, 1 U AmpliTaq Gold polymerase (Applied Biosystems, Foster City, Calif.), 200 µM of each dNTP, 4.5 mM $MgCl_2$ and AmpliTaq buffer to a final volume of 25 µl. The primer sequences used were as follows: ER-α: 5'-AGACATGAGAGCTGCCAACC-3' (SEQ ID NO: 5) (forward); 5'-GCCAGGCACATTCTAGAAGG-3' (SEQ ID NO: 6) (reverse). GAPDH: 5'-GGGTGTGAACCATGAGAAGT-3' (SEQ ID NO: 7) (forward); 5'-GACTGTGGTCATGAGTCCT-3' (SEQ ID NO: 8) (reverse). Samples were amplified with 40 cycles of denaturation at 95° C. for 30 sec, annealing at 58° C. for 30 sec, and extension at 72° C. for 30 sec for ER-α and GAPDH, respectively.

ER-α positive (MCF-7 cell line) and negative (MCA melanoma cell line) controls and reagent controls for RT-PCR assays were included as previously described (46). All PCR products were separated on 1.5% Tris-borate EDTA agarose gels for ER-α and 2% Tris-borate EDTA agarose gels for GAPDH and stained with SYBR Gold (Invitrogen Detection Techonologies, Eugene, Oregon). Each assay was repeated in triplicate.

Biostatistical Analysis

The correlation between ER-α methylation status of primary and metastatic melanomas with AJCC stage was assessed using the Chi square method. Similarly, the correlation between ER-α methylation status of circulating serum DNA with known clinical prognostic factors and BC response was assessed by the Chi square method. Additionally, a multivariate logistic regression model was developed to correlate clinical prognostic factors and serum circulating ER-α methylation status with response to BC.

Survival length was determined from the first day of BC treatment to death or the date of last clinical follow-up. Survival curves were derived using the Kaplan-Meier method and the differences between curves were analyzed using the log-rank test. Cox's proportional hazards regression model was used for multivariate analyses. Age, gender, ECOG (Eastern Cooperative Oncology Group) status, lactate dehydrogenase (LDH) level, number of metastasis sites, and ER-α methylation status were included in the multivariate model using a stepwise method for variable selection.

Results

Detection of Methylated ER-α DNA in Cell Lines

Initially, ER-α in established metastatic melanoma cell lines was assessed. The frequency of hypermethylated ER-α in metastatic melanoma cell lines was 91% (10 of 11). Among these lines, six had only a methylated-specific peak while four cell lines demonstrated both methylated- and unmethylated-specific peaks. These experiments optimized the MSP assay for ER-α and demonstrated the high frequency of hypermethylated ER-α in metastatic melanoma cells cultured in vitro.

ER-α re-expression with 5-Aza and TSA Treatment

Figure 1:
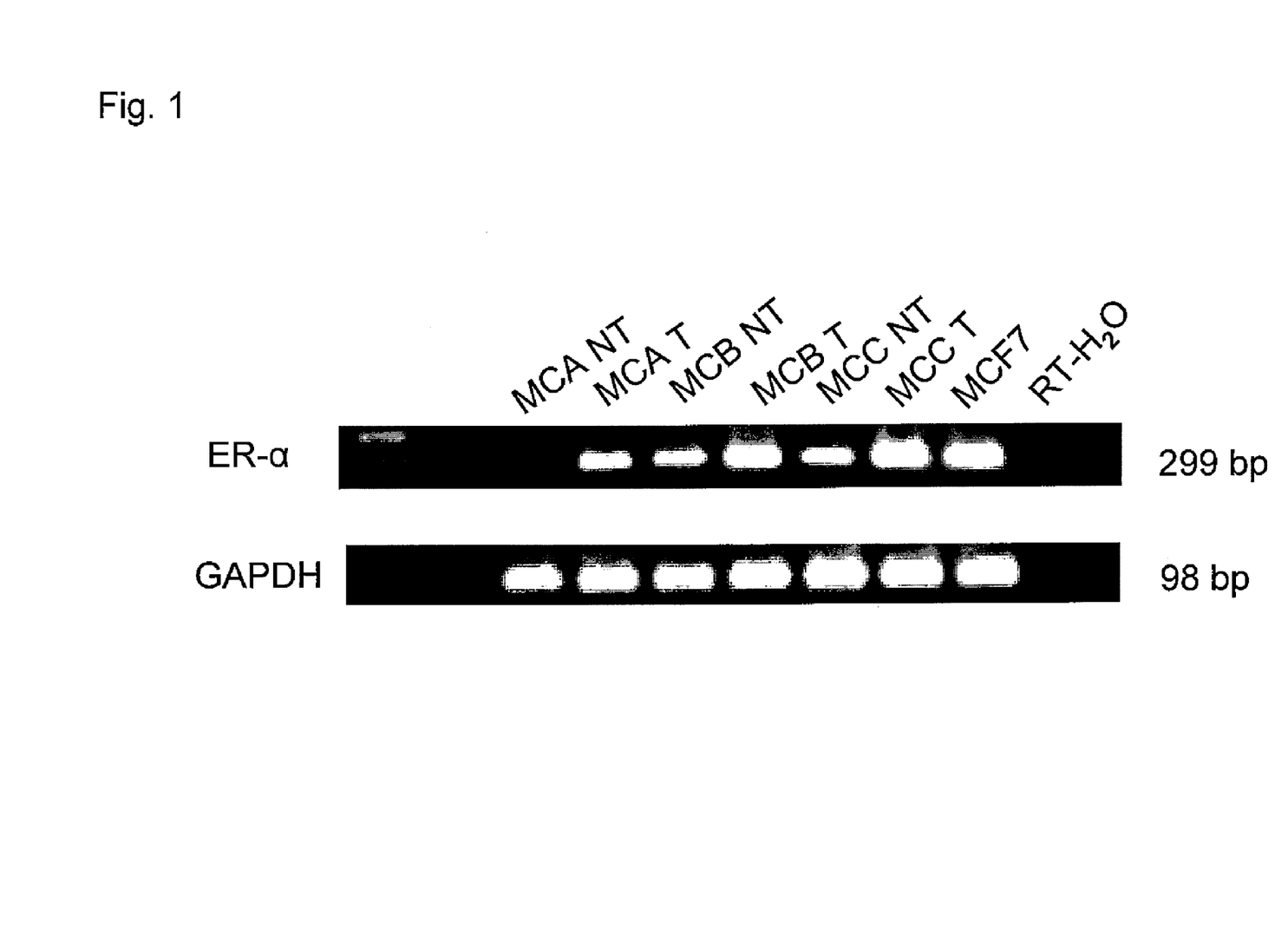
FIG. 1 shows representative expression and re-expression of ER-α in three melanoma lines (MCA, MCB, MCC) treated with 5-Aza (5-aza-2-deoxycytidine) and TSA (trichostatin A). mRNA expression was analyzed by RT-PCR (reverse-transcription polymerase chain reaction). The housekeeping gene GAPDH (glyceraldehyde-3-phosphate dehydrogenase) was included as a RT-PCR control. NT: cell line not treated with 5-Aza and TSA. T: cell line treated with 5-Aza and TSA.
Figure 2:
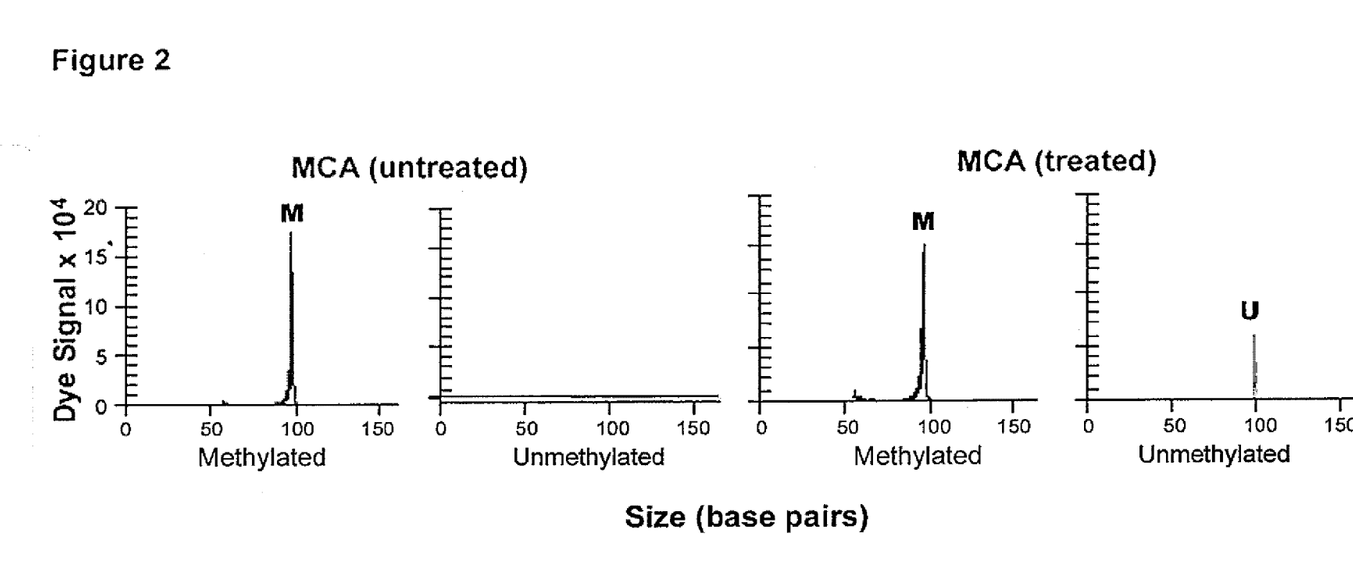
FIG. 2 depicts representative MSP (methylation-specific polymerase chain reaction) results of melanoma cell line (MCA) with and without 5-Aza plus TSA treatment. M: methylated-specific product. U: unmethylated-specific product. Only a methylated peak was initially observed (untreated). An unmethylated peak appeared after treatment with 5-Aza plus TSA (treated).

To determine if cells with hypermethylated ER-α can be induced to re-express ER-α mRNA, cell lines were treated with 5-Aza and TSA. In untreated cell lines, ER-α mRNA was detected in MCB, and MCC, but not MCA (FIG. 1). ER-α mRNA expression was restored to a detectable level in MCA after 5-Aza and TSA treatment (FIG. 1). After treatment with 5-Aza for five days followed by treatment with TSA for 24 hr, the MCA showed an unmethylated-specific DNA peak when assessed by MSP (FIG. 2). To further verify hypermethylation of the ER-α gene promoter region in melanoma, purified PCR products after sodium bisulfite modification were directly sequenced using a CEQ DYE Terminator Cycle Sequencing Kit (Beckman Coulter, Inc.). Promoter region CpG islands were fully methylated in the MCA cell line, which does not express ER-α, whereas MCC, a cell line that expresses ER-α, showed no evidence of promoter region CpG island hypermethylation. With an optimized assay for the detection of methylated ER-α, and demonstration that reversal of methylation leads to re-expression of ER-α mRNA, the detection of methylated ER-α was approached in PE melanoma specimens.

Detection of Methylated ER-α in Melanomas

Figure 3:
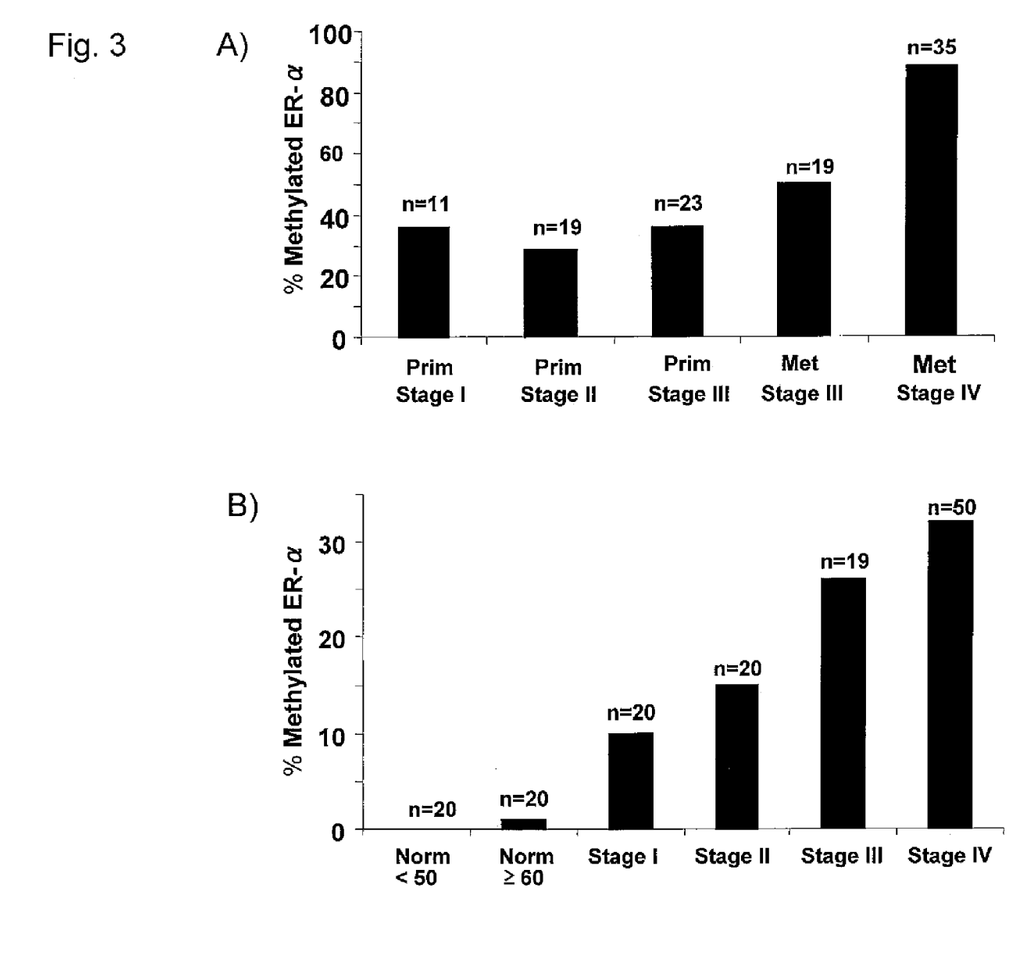
FIG. 3. A. The frequency of methylated ER-α DNA in melanoma tumors according to AJCC (American Joint Committee on Cancer) stage. Prim: Primary melanoma tumor. Met: Metastatic melanoma tumor. B. The frequency of methylated ER-α DNA in melanoma patients' sera according to AJCC stage. Norm<50: Normal healthy volunteers younger than 50 years. Norm≧60: Normal healthy volunteers aged 60 years or older.

53 PE primary melanomas (stage I, n=11; stage II, n=19; stage III, n=23) were evaluated using MSP. Overall, the frequency of methylation ER-α in primary melanomas was 32% (17 of 53). Similar rates of methylated ER-α were detected in primary tumors among the patients assessed, regardless of stage. The frequency of ER-α methylation in AJCC stage I, II, and III primary melanoma tumors was 36% (4 of 11), 26% (5 of 19), and 35% (8 of 23), respectively (FIG. 3A).

Additionally, 54 PE metastatic melanomas were assessed, including stage III lymph node metastases (n=19) and stage IV distant metastases (n=35; 14 subcutaneous, 9 lymph nodes, 6 lung, 5 colorectal, and 1 liver). Methylated ER-α was detected in 42% (8 of 19) of stage III and 86% (30 of 35) of IV metastatic melanomas (FIG. 3A). The frequency of methylated ER-α detected in stage IV metastatic tumors was significantly higher than in stage III metastatic tumors (p=0.0003). Overall, ER-α was methylated in 70% (38 of 54) of metastatic tumors, a more than two-fold increase in frequency compared to primary melanomas.

ER-α methylation status was also determined for 10 PE normal tissues from various organ sites (pancreas, n=2; liver, n=2; thymus, n=2; lung, n=2; and skin, n=2). Methylated ER-α was detected in 90% (9 of 10) of normal tissues, indicating that ER-α is usually methylated and silenced in normal tissue.

Because methylated ER-α in PE primary and metastatic melanomas was frequently detected, the detection of methylated ER-α in the serum of AJCC stage I-IV melanoma patients was assessed to evaluate its role as a blood marker for disease detection.

Detection of Circulating Methylated ER-α DNA in Serum

Figure 4:
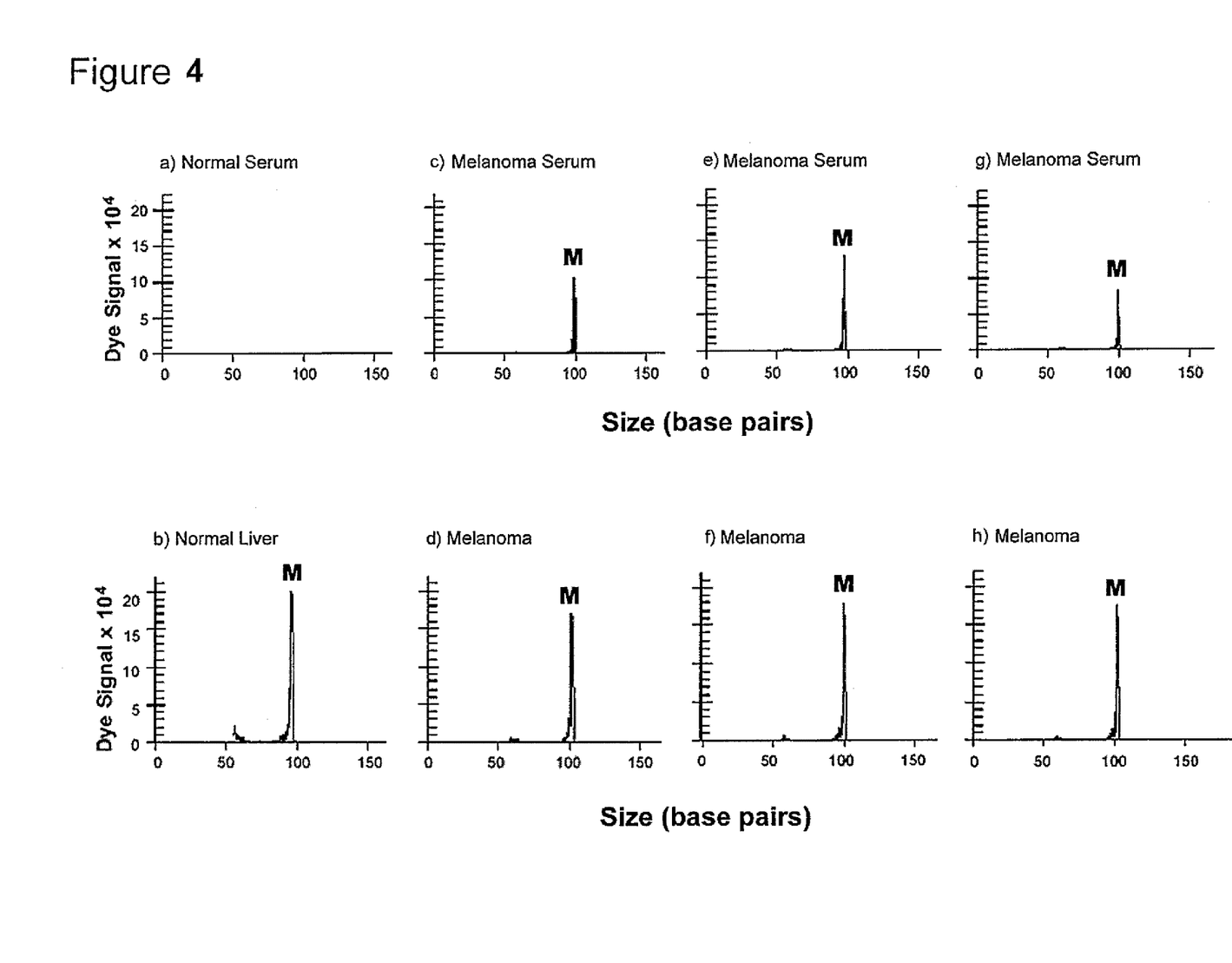

Previously, it was showed that circulating methylated DNA markers can be valuable surrogates of tumor progression (11, 44). Hence, an optimized assay was developed to detect the presence of free circulating methylated ER-α DNA in serum. The frequency with which methylated ER-α was detected in serum increased with tumor progression and according to AJCC stage. In the analysis of 109 melanoma patients' sera, the frequency of circulating methylated ER-α in AJCC stage I, II, III, and IV sera was 10% (2 of 20), 15% (3 of 20), and 26% (5 of 19), and 32% (16 of 50), respectively (FIG. 3B). The frequency of serum methylated ER-α was increased in patients with more advanced disease; methylated ER-α was detected in stage III/IV more frequently than in stage I/II (p=0.034). Methylated ER-α was detected in the sera of only 1 of 40 healthy normal donors, an 82 year old female. Representative methylation peaks from normal donor sera, normal liver tissue, melanoma patient sera, and melanoma tumors are provided in FIG. 4. Healthy normal donors ranged in age from 20 to 84 (mean, 56); the gender distribution of normal volunteers was comparable to that of melanoma patients assessed. Having established that methylated ER-α can be reliably detected in the sera of melanoma patients but not in normal volunteers, and is a marker of disease progression, attention was focused on assessing the clinical utility of methylated ER-α as a predictor of disease outcome.

Clinical Utility of Circulating Methylated ER-α

Prior to receiving systemic concurrent BC, blood from AJCC stage IV melanoma patients was obtained and retrospectively assayed for the detection of circulating methylated ER-α DNA. Serum ER-α methylation from stage IV patients was assessed to predict the patients most likely to respond to BC. The median time of clinical follow-up after the initial blood draw was 12.5 months. The frequency of circulating methylated ER-α for responders (4 of 23, 17%) was significantly lower (p=0.018) than non-responders (12 of 24, 50%). In a multivariate logistic regression model that included known clinical prognostic factors for melanoma, the presence of circulating serum methylated ER-α DNA was the only factor that significantly correlated with response to BC (OR=0.21, 95% CI=0.06 to 0.81; p=0.023). Patients categorized as BC responders had significantly better overall survival compared to patients deemed BC non-responders (Log Rank, p<0.0001).

Regardless of response to BC, patients with serum methylated ER-α had significantly worse progression-free survival compared to patients in whom methylated ER-α was not detected (Log Rank, p=0.002). Serum methylated ER-α, LDH>190 IU/L and age<50 were significantly correlated with progression-free survival in a univariate analysis (Log Rank; methylated ER-α, p=0.002; LDH>190 IU/L, p=0.013; age<50, p=0.028).

Similarly, patients with circulating methylated ER-α had significantly worse overall survival compared to patients in whom methylated ER-α was not detected (Log Rank, p=0.002). Circulating methylated ER-α and serum LDH>190 IU/L significantly correlated with overall survival (Log Rank; methylated ER-α, p=0.002; LDH>190 IU/L, p=0.015). Other prognostic factors (gender, age, ECOG, and the number of metastatic sites) were not significant.

Figure 5:
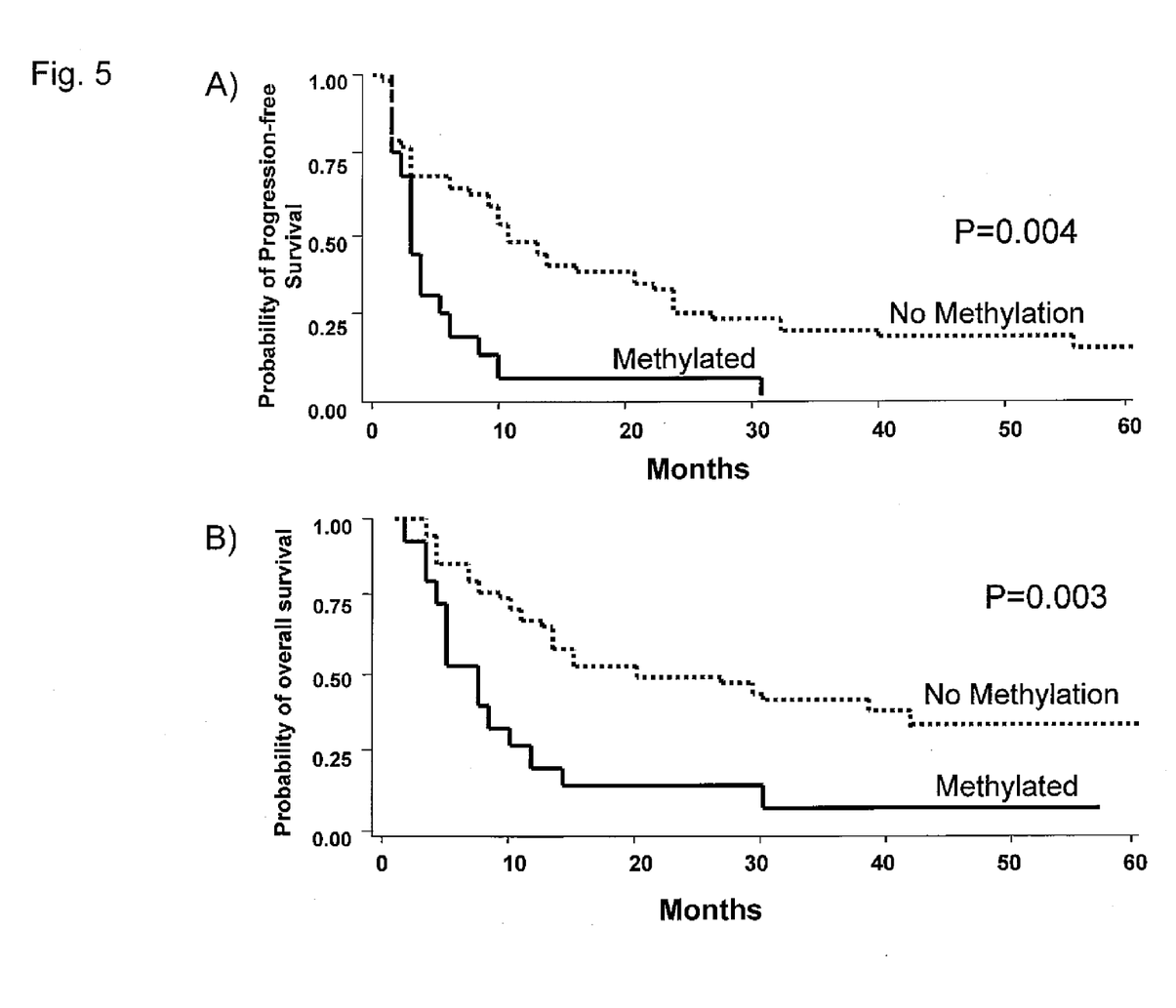
FIG. 5. A. Kaplan-Meier curves showing the correlation of pre-BC (biochemotherapy) serum ER-α methylation status with progression-free survival (Cox proportional hazard, p=0.004). Methylated: Patients with serum methylated ER-α DNA; No methylation: Patients with no detectable serum methylated ER-α. B. Kaplan-Meier curves showing the correlation of pre-BC serum ER-α methylation status with overall survival (Cox proportional hazard, p=0.003). Methylated: Patients with serum methylated ER-α; No methylation: Patients with no detectable serum methylated ER-α.

A multivariate Cox's proportional hazard regression model was developed to correlate clinical factors and ER-α methylation status with progression-free and overall survival. Age, gender, ECOG status, LDH level, number of metastasis sites, and ER-α methylation status were included in the model using a stepwise method for variable selection. Serum methylated ER-α was the only independent factor predicting progression-free (FIG. 5A; RR 2.64, 95% CI 1.36-5.13, p=0.004) and overall survival (FIG. 5B; RR 2.31, 95% CI 1.41-5.58, p=0.003).

Methylated ER-α: Gender and Age

Because ER-α hypermethylation is influenced by both age and gender in other cancers, the relation of these factors to methylated ER-α status in primary and metastatic melanomas and serum was assessed. There was no significant difference in the frequency of methylated ER-α in PE tumors or sera between male and female patients, nor was there any significant difference in the frequency of methylated ER-α in tumors between patients≧60 years old and patients<50 years old.

Discussion

Methylated ER-α has been detected in neoplasia of the colorectum, lung, and breast (21, 22, 24, 26, 27). The reported expression level of ER-α in melanoma has been variable, with several studies failing to demonstrate the presence of ER-α using monoclonal antibodies (28-31). Tamoxifen has been used in chemotherapy and BC regimens for over a decade (36-39). Although improved response rates have been reported with its use, tamoxifen has not been shown to significantly improve overall survival in advanced melanoma (40, 41). This is the first study reporting a potential mechanism for the failure of tamoxifen in the treatment of melanoma. It has been shown that the variable down-regulation of ER in melanoma is due to epigenetic control of its expression via gene promoter region hypermethylation.

These studies demonstrate that methylated ER-α can be detected in melanoma cell lines and ER-α mRNA expression can be re-established after demethylation with 5-Aza and TSA. Additionally, methylated ER-α can be detected in PE primary and metastatic melanoma tumors, demonstrating its value as a biomarker of tumor progression. Methylated ER-α DNA was detected in the serum of melanoma patients with AJCC stage I-IV disease and was a biomarker of disease progression. Furthermore, serum circulating hypermethylated ER-α in AJCC stage IV melanoma patients predicted response to BC, progression-free survival, and overall survival.

The in vitro experiments demonstrated that all but one of the 11 metastatic melanoma cell lines assayed had methylated ER-α. This suggests that in vitro culturing may promote the epigenetic silencing of ER-α or select for a subpopulation of cells with methylated ER-α. 5-Aza alone did not significantly increase ER-α mRNA expression (data not shown); the histone deacetylase inhibitor TSA was necessary to significantly increase expression above pretreatment levels. A HDAC inhibitor, such as TSA, modulates chromatin histones and, together with 5-Aza can effectively activate gene expression. That TSA treatment was a necessary step for ER-α mRNA re-expression suggests histone acetylation also plays an important regulatory role in ER-α expression (26, 27). Similar epigenetic regulation in breast cancer, ovarian cancer, prostate cancer, and hepatocellular cancer has been reported (3, 23).

The frequency of ER-α methylation served as a marker of progression from primary to metastatic disease and from regional nodal metastasis to distant visceral metastasis. As with breast cancer, the expression of ER-α mRNA as regulated by ER-α methylation is directly or indirectly related to the development of metastasis.

Because methylated ER-α in primary and metastatic melanomas was able to be detected, whether or not methylated ER-α could function as a blood-based biomarker for diagnosis and disease surveillance was assessed. In the current study, methylated ER-α was detected in the serum of AJCC stage I-IV melanoma patients in a pattern related to disease progression. In a subset of matched melanoma tumor and serum sample pairs, all patients with methylated DNA detected in serum had primary or metastatic tumors with methylated ER-α as well (data not shown).

Knowing that methylated ER-α in serum could be detected, the predictive utility of this marker in a selected population of stage IV melanoma patients enrolled in a concurrent BC trial was assessed. Prediction of the response to therapy based on the methylation status of circulating ER-α was attempted. Response rates for systemic therapies in advanced metastatic melanoma are alarmingly low. BC, the use of chemotherapy in conjunction with immune modulators, has produced better response rates (40-42), but outcomes differ greatly between responders and non-responders. It has been difficult to predict tumor response before or in the early phases of BC. Identifying molecular predictors of therapeutic response may permit physicians to treat those patients most likely to respond to therapy while sparing non-responsive patients unnecessary treatment and its associated morbidity. Methylated ER-α was more commonly detected in the serum of patients who failed to respond to BC and was the only factor predictive of response to BC. Serum methylated ER-α was the only independent predictor of progression-free and overall survival in a multivariate analysis, surpassing even known clinical prognostic factors.

There are several possible explanations for these findings. First, tamoxifen, a member of the selective estrogen receptor modulator family, was used in the BC regimen of 44 out of 50 patients. Patients without serum methylated ER-α, who therefore express ER-α, may be more likely to respond to the anti-tumor effects of tamoxifen. Conversely, the failure of patients to respond to BC may be partially explained by the inability of tamoxifen to exert its anti-tumor effects when ER-α expression is silenced due to promoter region hypermethylation. This is akin to the clinical situation seen in breast cancer, where tumors not expressing ER-α do not respond to hormone therapy and carry a poorer prognosis (23). ER-α methylation could also reflect a pathophysiological event that includes a more global hypermethylation of tumor-related genes, thereby providing tumor cells with a growth advantage (8).

Methylated ER-α is present in normal cells of different histology (47, 48). In the serum analysis, however, ER-α was not detected in the serum from normal healthy donors. Normal cells containing methylated ER-α would be expected to release this DNA into the bloodstream. Why, then, was methylated ER-α not detected in normal healthy donors? It is believed that methylated ER-α from tumors is cleared less efficiently than methylated ER-α from normal cells. The destruction of normal cells is primarily through apoptosis-related events, resulting in the release of small, characteristic enzyme-degraded fragments of DNA. As a result, the DNA released from normal cells is cleared rapidly and not readily detected in blood. On the contrary, tumor cells disrupted by physical trauma or cell necrosis release intact, large fragments of DNA (49). Melanoma patients release both free DNA and tumor cells into the blood stream. Circulating tumor cells may release large fragments of DNA due to non-apoptotic death mechanisms (unpublished results). The detection of methylated ER-α in melanoma patients strongly suggests that the circulating DNA is tumor-related.

Age-dependent methylation of ER-α has been previously implicated in other studies (50). In this study, age differences in ER-α methylation was not found. Among 40 healthy volunteers, methylated ER-α was detected only in one 82 year-old donor, which may be due to factors unrelated to aging, including subclinical cancer. Further detailed studies will validate the presence and significance of ER-α methylation in healthy elderly volunteers.

This is the first study demonstrating the detection of methylated ER-α in both melanoma patients' tumor tissues and sera. The detection of methylated ER-α in tumors or sera correlates with tumor progression, and is therefore prognostically important. These findings indicate that detection of methylated ER-α in serum may identify a population of patients with poor melanoma outcomes and poor response to systemic therapy in whom alternative treatment management should be considered. Furthermore, these data support the initiation of a prospective BC trial for stage IV melanoma based on serum ER-α methylation status. Such a trial would provide valuable information regarding the clinical value of tamoxifen in the treatment of melanoma and further test the ability of the ER-α methylation assay to predict response to BC.

REFERENCES

1. Balch C M, Soong S J, Atkins M B, et al. An evidence-based staging system for cutaneous melanoma. CA Cancer J Clin 2004, 54:131-49.
2. Dulaimi E, Hillinck J, Ibanez de Caceres I, Al-Saleem T, Cairns P. Tumor suppressor gene promoter hypermethylation in serum of breast cancer patients. Clin Cancer Res 2004, 10:6189-93.
3. Jeronimo C, Henrique R, Hoque M O, et al. A quantitative promoter methylation profile of prostate cancer. Clin Cancer Res 2004, 10:8472-8.
4. Lapidus R G, Ferguson A T, Ottaviano Y L, et al. Methylation of estrogen and progesterone receptor gene 5' CpG islands correlates with lack of estrogen and progesterone receptor gene expression in breast tumors. Clin Cancer Res 1996, 2:805-10.
5. Shinozaki M, Hoon D S, Giuliano A E, et al. Distinct hypermethylation profile of primary breast cancer is associated with sentinel lymph node metastasis. Clin Cancer Res 2005, 11:2156-62.
6. Umetani N, Mori T, Koyanagi K, et al. Aberrant hypermethylation of ID4 gene promoter region increases risk of lymph node metastasis in T1 breast cancer. Oncogene 2005, 24:4721-7.
7. Herman J G, Baylin S B. Gene silencing in cancer in association with promoter hypermethylation. N Engl J Med 2003, 349:2042-54.
8. Jones P A, Baylin S B. The fundamental role of epigenetic events in cancer. Nat Rev Genet 2002, 3:415-28.
9. Sidransky D. Emerging molecular markers of cancer. Nat Rev Cancer 2002, 2:210-9.
10. Spugnardi M, Tommasi S, Dammann R, Pfeifer G P, Hoon D S. Epigenetic inactivation of RAS association domain family protein 1 (RASSF1A) in malignant cutaneous melanoma. Cancer Res 2003, 63:1639-43.
11. Hoon D S, Spugnardi M, Kuo C, Huang S K, Morton D L, Taback B. Profiling epigenetic inactivation of tumor suppressor genes in tumors and plasma from cutaneous melanoma patients. Oncogene 2004, 23:4014-22.
12. Fujimoto A, O'Day S J, Taback B, Elashoff D, Hoon D S. Allelic imbalance on 12q22-23 in serum circulating DNA of melanoma patients predicts disease outcome. Cancer Res 2004, 64:4085-8.
13. Fujiwara Y, Chi D D, Wang H, et al. Plasma DNA microsatellites as tumor-specific markers and indicators of tumor progression in melanoma patients. Cancer Res 1999, 59:1567-71.
14. Hoon D S, Bostick P, Kuo C, et al. Molecular markers in blood as surrogate prognostic indicators of melanoma recurrence. Cancer Res 2000, 60:2253-7.
15. Nakayama T, Taback B, Nguyen D H, et al. Clinical significance of circulating DNA microsatellite markers in plasma of melanoma patients. Ann N Y Acad Sci 2000, 906:87-98.
16. Taback B, Hoon D S. Circulating nucleic acids and proteomics of plasma/serum: clinical utility. Ann NY Acad Sci 2004, 1022:1-8.
17. Taback B, O'Day S J, Boasberg P D, et al. Circulating DNA microsatellites: molecular determinants of response to biochemotherapy in patients with metastatic melanoma. J Natl Cancer Inst 2004, 96:152-6.
18. Beato M, Herrlich P, Schutz G. Steroid hormone receptors: many actors in search of a plot. Cell 1995, 83:851-7.

19. Mangelsdorf D J, Thummel C, Beato M, et al. The nuclear receptor superfamily: the second decade. Cell 1995, 83:835-9.
20. Bonkhoff H, Fixemer T, Hunsicker I, Remberger K. Estrogen receptor expression in prostate cancer and premalignant prostatic lesions. Am J Pathol 1999, 155:641-7.
21. Fujii S, Tominaga K, Kitajima K, et al. Methylation of the oestrogen receptor gene in non-neoplastic epithelium as a marker of colorectal neoplasia risk in longstanding and extensive ulcerative colitis. Gut 2005, 54:1287-92.
22. Jensen E V, Cheng G, Palmieri C, et al. Estrogen receptors and proliferation markers in primary and recurrent breast cancer. Proc Natl Acad Sci USA 2001, 98:197-202.
23. Lapidus R G, Nass S J, Davidson N E. The loss of estrogen and progesterone receptor gene expression in human breast cancer. J Mammary Gland Biol Neoplasia 1998, 3:85-94.
24. Leu Y W, Yan P S, Fan M, et al. Loss of estrogen receptor signaling triggers epigenetic silencing of downstream targets in breast cancer. Cancer Res 2004, 64:8184-92.
25. O'Neill P A, Davies M P, Shaaban A M, et al. Wild-type oestrogen receptor beta (ERbeta1) mRNA and protein expression in Tamoxifen-treated post-menopausal breast cancers. Br J Cancer 2004, 91:1694-702.
26. Yang X, Ferguson A T, Nass S J, et al. Transcriptional activation of estrogen receptor alpha in human breast cancer cells by histone deacetylase inhibition. Cancer Res 2000, 60:6890-4.
27. Yang X, Phillips D L, Ferguson A T, Nelson W G, Herman J G, Davidson N E. Synergistic activation of functional estrogen receptor (ER)-alpha by DNA methyltransferase and histone deacetylase inhibition in human ER-alpha-negative breast cancer cells. Cancer Res 2001, 61; 7025-9.
28. Cohen C, DeRose P B, Campbell W G, Schlosnagle D C, Sgoutas D. Estrogen receptor status in malignant melanoma. Am J Dermatopathol 1990, 12:562-4.
29. Fisher R I, Neifeld J P, Lippman M E. Oestrogen receptors in human malignant melanoma. Lancet 1976, 2:337-9.
30. Flowers J L, Seigler H F, McCarty K S, Sr., Konrath J, McCarty K S, Jr. Absence of estrogen receptor in human melanoma as evaluated by a monoclonal antiestrogen receptor antibody. Arch Dermatol 1987, 123:764-5.
31. Walker M J, Beattie C W, Patel M K, Ronan S M, Das Gupta T K. Estrogen receptor in malignant melanoma. J Clin Oncol 1987, 5:1256-61.
32. Gill P G, De Young N J, Thompson A, Keightley D D, Horsfall D J. The effect of tamoxifen on the growth of human malignant melanoma in vitro. Eur J Cancer Clin Oncol 1984, 20:807-15.
33. Kanter-Lewensohn L, Girnita L, Girnita A, et al. Tamoxifen-induced cell death in malignant melanoma cells: possible involvement of the insulin-like growth factor-1 (IGF-1) pathway. Mol Cell Endocrinol 2000, 165:131-7.
34. Cocconi G, Bella M, Calabresi F, et al. Treatment of metastatic malignant melanoma with dacarbazine plus tamoxifen. N Engl J Med 1992, 327:516-23.
35. Flaherty L E, Liu P Y, Mitchell M S, et al. The addition of tamoxifen to dacarbazine and cisplatin in metastatic malignant melanoma. A phase II trial of the Southwest Oncology Group, (SWOG-8921). Am J Clin Oncol 1996, 19:108-13.
36. Rumke P, Kleeberg U R, MacKie R M, et al. Tamoxifen as a single agent for advanced melanoma in postmenopausal women. A phase II study of the EORTC Malignant Melanoma Cooperative Group. Melanoma Res 1992, 2:153-6.
37. Falkson C I, Ibrahim J, Kirkwood J M, Coates A S, Atkins M B, Blum R H. Phase III trial of dacarbazine versus dacarbazine with interferon alpha-2b versus dacarbazine with tamoxifen versus dacarbazine with interferon alpha-2b and tamoxifen in patients with metastatic malignant melanoma: an Eastern Cooperative Oncology Group study. J Clin Oncol 1998, 16:1743-51.
38. Agarwala S S, Ferri W, Gooding W, Kirkwood J M. A phase III randomized trial of dacarbazine and carboplatin with and without tamoxifen in the treatment of patients with metastatic melanoma. Cancer 1999, 85:1979-84.
39. Chiarion Sileni V, Nortilli R, Aversa S M, et al. Phase II randomized study of dacarbazine, carmustine, cisplatin and tamoxifen versus dacarbazine alone in advanced melanoma patients. Melanoma Res 2001, 11:189-96.
40. O'Day S J, Gammon G, Boasberg P D, et al. Advantages of concurrent biochemotherapy modified by decrescendo interleukin-2, granulocyte colony-stimulating factor, and tamoxifen for patients with metastatic melanoma. J Clin Oncol 1999, 17:2752-61.
41. O'Day S J, Boasberg P D, Piro L, et al. Maintenance biotherapy for metastatic melanoma with interleukin-2 and granulocyte macrophage-colony stimulating factor improves survival for patients responding to induction concurrent biochemotherapy. Clin Cancer Res 2002, 8:2775-81.
42. O'Day S J, Atkins M B, Weber J. A phase II multi-center trial of maintenance biotherapy (MBT) after induction concurrent biochemotherapy (BCT) for patients (Pts) with metastatic melanoma. In: Proc ASCO 2005, pp. 710s.
43. Takeuchi H, Morton D L, Kuo C, et al. Prognostic significance of molecular upstaging of paraffin-embedded sentinel lymph nodes in melanoma patients. J Clin Oncol 2004, 22:2671-80.
44. Mori T, O'Day S J, Umetani N, et al. Predictive utility of circulating methylated DNA in serum of melanoma patients receiving biochemotherapy. J Clin Oncol 2005, 23:9351-8.
45. Umetani N, de Maat M F, Mori T, Takeuchi H, Hoon D S. Synthesis of universal unmethylated control DNA by nested whole genome amplification with phi29 DNA polymerase. Biochem Biophys Res Commun 2005, 329:219-23.
46. Koyanagi K, O'Day S J, Gonzalez R, et al. Serial monitoring of circulating melanoma cells during neoadjuvant biochemotherapy for stage III melanoma: outcome prediction in a multicenter trial. J Clin Oncol 2005, 23:8057-64.
47. Liu L, Zhang J, Bates S, et al. A methylation profile of in vitro immortalized human cell lines. Int J Oncol 2005, 26:275-85.
48. Zhao C, Lam E W, Sunters A, et al. Expression of estrogen receptor beta isoforms in normal breast epithelial cells and breast cancer: regulation by methylation. Oncogene 2003, 22:7600-6.
49. Hiramatsu S, Umetani N, Amersi F, Martino S, Giuliano A E, Hoon D S. Prediction of breast metastasis by integrity of free circulating DNA in serum. Clin Chem 2005, 51:25.
50. Li L C, Shiina H, Deguchi M, et al. Age-dependent methylation of ESR1 gene in prostate cancer. Biochem Biophys Res Commun 2004, 321:455-61.

EXAMPLE II

ER-α Methylation in Breast, Pancreatic, and Colon Caner

Methylation of the ER-α gene promoter in circulating acellular DNA has been detected in breast cancer (about 30%), pancreatic cancer (39 of 50; 78%), and colon cancer (15 of 63; 24%) patients, respectively.

The contents of all references cited herein are incorporated by reference in their entirety.

What is claimed is:

1. A method of determining whether a human subject is suffering from melanoma cancer, comprising:
   providing a serum-sample from a human subject suspected of having melanoma cancer;
   isolating an acellular DNA sample from the serum sample;
   determining the methylation level of the estrogen receptor-alpha (ER-α) gene promoter in the acellular DNA sample; and
   determining that the human subject is suffering from melanoma cancer when the methylation level of the ER-α gene promoter in the acellular DNA sample is higher than a control methylation level.

2. The method of claim 1, wherein the melanoma cancer is a primary or metastatic melanoma cancer.

3. A method of predicting survival in a human subject suffering from melanoma cancer, comprising:
   providing a serum sample from a human subject having melanoma cancer;
   isolating an acellular DNA sample from the serum sample;
   determining the methylation level of the ER-α gene promoter in the acellular DNA sample; and
   predicting a shorter survival when the methylation level of the ER-α gene promoter in the acellular DNA sample is higher than a control methylation level.

4. The method of claim 3, wherein the shorter survival is a shorter progression-free survival or overall survival.

5. The method of claim 3, wherein the melanoma cancer is a primary or metastatic melanoma cancer.

6. A method of predicting tumor progression in a human subject having melanoma cancer, comprising:
   providing a melanoma cancer tumor tissue sample of the human subject having melanoma cancer;
   isolating a cellular DNA sample from the melanoma cancer tumor tissue sample;
   determining the methylation level of the ER-α gene promoter in the cellular DNA sample;
   predicting a more advanced tumor progression when the methylation level of the ER-α gene promoter in the cellular DNA sample is higher than a control methylation level.

7. The method of claim 6, wherein the melanoma cancer is a primary or metastatic melanoma cancer.

8. A method of predicting tumor progression in a human subject having melanoma cancer, comprising:
   providing a serum sample from the human subject having melanoma cancer;
   isolating an acellular DNA sample from the serum sample;
   determining the methylation level of the ER-α gene promoter in the acellular DNA sample;
   predicting a more advanced tumor progression when the methylation level of the ER-α gene promoter in the acellular DNA sample is higher than a control methylation level.

9. The method of claim 3, further comprising predicting a poor response to biochemotherapy (BC) when the subject having melanoma cancer has a methylation level of the ER-α gene promoter in the sample DNA that is higher than a control methylation level.

* * * * *